United States Patent [19]

Brewster et al.

[11] Patent Number: 4,772,625

[45] Date of Patent: Sep. 20, 1988

[54] 1,3-DIOXAN-5-YL-HEXENOIC ACIDS

[75] Inventors: Andrew G. Brewster; Michael J. Smithers, both of Macclesfield, United Kingdom

[73] Assignee: Imperial Chemical Industries PLC, London, England

[21] Appl. No.: 861,330

[22] Filed: May 9, 1986

[30] Foreign Application Priority Data

May 10, 1985 [GB] United Kingdom ............... 8511891

[51] Int. Cl.$^4$ .................. A61K 31/335; C07D 319/06
[52] U.S. Cl. ..................................... 514/452; 549/375
[58] Field of Search ..................... 549/375; 514/452

[56] References Cited

U.S. PATENT DOCUMENTS 4,567,197 1/1986 Brewster et al. ................ 514/452

FOREIGN PATENT DOCUMENTS

| 0094239 | 11/1983 | European Pat. Off. . |
| 0142323 | 5/1985 | European Pat. Off. . |
| 0142324 | 5/1985 | European Pat. Off. . |
| 0145260 | 6/1985 | European Pat. Off. . |

Primary Examiner—Nicky Chan
Attorney, Agent, or Firm—Cushman, Darby & Cushman

[57] ABSTRACT

The invention provides a novel group of 4(Z)-6-([2,4,5-cis]-2-alkyl-4-o-hydroxyphenyl-1,3-dioxan-5-yl)hexenoic acids of formula I wherein R is branched alkyl of 3-5 carbon atoms and one of X and Y is hydrogen or fluoro and the other is hydrogen, and their pharmaceutically acceptable salts; together with their pharmaceutical compositions for use in treating a variety of disease conditions. Also provided are methods for the manufacture of the novel compounds. A representative compound is that in which R is t-butyl ans X and Y are both hydrogen.

8 Claims, No Drawings

1,3-DIOXAN-5-YL-HEXENOIC ACIDS

This invention concerns novel hexenoic acids and, more particularly, novel 4-(Z)-6-([2,4,5-cis]-2-alkyl-4-o-hydroxyphenyl-1,3-dioxan-5-yl)-hexenoic acids which antagonise one or more of the actions of thromboxane $A_2$ (hereafter referred to as "$TXA_2$") and which are of value as therapeutic agents.

It is known that $TXA_2$ is a potent aggregator of blood platelets and a powerful vasoconstrictor. $TXA_2$ is also a potent constrictor of bronchial and tracheal smooth muscle. $TXA_2$ may therefore be involved in a wide variety of disease conditions, for example ischaemic heart disease such as myocardial infarction, angina, cerebrovascular disease such as transient cerebral ischaemia, migraine and stroke, peripheral vascular disease such as atherosclerosis, microangiopathy, hypertension and blood clotting defects due to lipid imbalance, and pulmonary disease such as pulmonary embolism, bronchial asthma, bronchitis, pneumonia, dyspnoea and emphysema. Accordingly, compounds which antagonise the actions of $TXA_2$ may be expected to have therapeutic value in the prevention or treatment of any one or more of the above mentioned diseases or any other disease conditions in which it is desirable to antagonise the actions of $TXA_2$.

It is also known from our European patent application, publication No. 94239, that 4-phenyl-1,3-dioxan-5-ylalkenoic acid derivatives of the formula Z having cis relative stereochemistry at positions 4 and 5 of the dioxane ring and wherein Ra and Rb are variously hydrogen, alkyl, halogenoalkyl, alkenyl and optionally substituted aryl or arylalkyl, Rc is hydroxy, alkoxy or alkanesulphonamido, n is 1 or 2, A is ethylene or vinylene, Y is (2-5C)polymethylene optionally substituted by alkyl and benzene ring B bears one or two optional substituents, possess the property of antagonising one or more of the actions of $TXA_2$. We have now discovered and herein lies the basis of our invention that particularly useful $TXA_2$ antagonism is shown by a novel group of compounds of formula Z in which Ra is branched (3-5C)alkyl, Rb is hydrogen, benzene ring B is o-hydroxyphenyl, n is 1, A is cis-vinylene, Y is ethylene and Rc is hydroxy.

According to the invention there is provided a hexenoic acid of the formula I set out hereinafter wherein R is branched alkyl of 3 to 5 carbon atoms; and one of X and Y is hydrogen or fluorine and the other is hydrogen; and wherein the groups at positions 2, 4 and 5 have cis-relative stereochemistry; or a pharmaceutically acceptable salt thereof.

It will be appreciated that the compounds of formula I possess asymmetric carbon atoms and may exist and be isolated in racemic and optically active forms. The invention includes both the racemic forms and any optically active form (or mixtures thereof) which is capable of antagonising one or more of the actions of $TXA_2$, it being well known in the art how to prepare individual optical isomers (for example by synthesis from optically active starting materials or resolution of a racemic form) and how to determine the $TXA_2$ antagonist properties using one or more of the standard tests referred to hereafter.

In the chemical formulae attached hereto, although a particular configuration is shown, this does not necessarily correspond to the absolute configuration.

Specific values for R which are of particular interest are, for example, isopropyl, isobutyl, sec-butyl and t-butyl.

A preferred value for X is hydrogen and for Y is hydrogen or fluoro.

A preferred group of compounds of the invention comprises those compounds of the formula I wherein X and Y are both hydrogen; together with the pharmaceutically acceptable salts thereof. A still more preferred group comprises those compounds of formula I described hereinafter in Examples 1, 2, 3, 4 or 7; together with the pharmaceutically acceptable salts thereof. A particularly preferred compound is that described in Example 1 or 7, or a pharmaceutically acceptable salt thereof.

Particular pharmaceutically acceptable salts of hexenoic acids of formula I are, for example, alkali metal and alkaline earth metal salts such as lithium, sodium potassium, magnesium and calcium salts, aluminium and ammonium salts, and salts with organic amines and quaternary bases forming physiologically acceptable cations such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

The compounds of formula I may be manufactured by conventional procedures of organic chemistry, well known in the art for the manufacture of structurally analogous compounds. Such procedures are provided as a further aspect of the invention and are illustrated by the following processes in which R, X, and Y have any of the meanings defined hereinabove:

(a) A phenol derivative of the formula II wherein R" is a suitable protecting group, for example (1-6C)alkyl (such as methyl or ethyl), acyl (such as acetyl, benzoyl, methanesulphonyl or p-toluenesulphonyl), allyl, tetrahydropyran-2-yl or trimethylsilyl, is deprotected.

The deprotection conditions used depend on the nature of the protecting group R". Thus, for example, when it is (1-6C)alkyl (and especially methyl), the deprotection may be carried out by heating with sodium thioethoxide in a suitable solvent (such as N,N-dimethylformamide or N,N-dimethyl-3,4,5,6-tetrahydro-2(1H)-pyrimidinone) at a temperature in the range, for example, 50° to 160° C. Alternatively, an ethyl or methyl protecting group may be removed by reaction with lithium diphenylphosphide in a suitable solvent (such as tetrahydrofuran or methyl t-butyl ether) at a temperature in the range, for example, 0° to 60° C. When the protecting group is acyl it may be removed, for example, by hydrolysis in the presence of a base (such as sodium or potassium hydroxide) in a suitable aqueous solvent [such as an aqueous (1-4C)alkanol or glycol] at a temperature in the range, for example, 10° to 60° C. When the protecting group is allyl or tetrahydropyran-2-yl it may be removed for example by treatment with strong acid such as trifluoroacetic acid and when it is trimethylsilyl, it may be removed, for example, by reaction with aqueous tetrabutylammonium fluoride or sodium fluoride using a conventional procedure.

(b) An aldehyde of the formula III is reacted with a Wittig reagent of the formula $R'_3P=CH.(CH_2)_2.CO_2^-M^+$ wherein R' is (1-6C)alkyl or aryl (especially phenyl) and $M^+$ is a cation, for example an alkali metal cation such as the lithium, sodium or potassium cation.

The process in general produces the required compounds of formula I in which the substituents adjacent to the double bond have predominantly cis-relative stereochemistry i.e. the "Z" isomer. However the process also produces analogous compounds having trans-relative stereochemistry which may be removed by a conventional procedure such as chromatography or crystallisation.

The process is conveniently performed in a suitable solvent or diluent, for example an aromatic solvent such as benzene, toluene or chlorobenzene, an ether such as 1,2-dimethoxyethane, t-butyl methyl ether, dibutyl ether or tetrahydrofuran, in dimethyl sulphoxide or tetramethylene sulphone, or in a mixture of one or more such solvents or diluents. The process is generally performed at a temperature in the range, for example, −80° C. to 40° C. but is conveniently performed at or near room temperature, for example in the range 0° to 35° C.

(c) An erythro-diol derivative of the formula IV wherein one of $Q^1$ and $Q^2$ is hydrogen and the other is hydrogen or a group of the formula —CRaRb.OH (wherein Ra and Rb are the same or different (1-4C) alkyl) is reacted with an aldehyde of the formula R.CHO, or an acetal, hemiacetal or hydrate thereof.

The aldehyde [or its hydrate, or its acetal or hemiacetal with a (1-4C)alkanol (such as methanol or ethanol)] may conveniently be present in an excess.

The reaction is generally performed in the presence of an acid catalyst such as hydrogen chloride, hydrogen bromide, sulphuric acid, phosphoric acid, methanesulphonic acid, p-toluenesulphonic acid or an acidic polymer, conveniently in the presence of a suitable solvent or diluent, such as toluene, xylene or an ether, for example tetrahydrofuran, dibutyl ether, methyl t-butyl ether or 1,2-dimethoxyethane, and at a temperature in the range, for example 0° to 80° C.

Those starting materials of formula IV wherein $Q^1$ and $Q^2$ are both hydrogen may be obtained, for example, by mild, acid catalysed, hydrolysis or alcoholysis of the dioxane ring of a compound of formula V wherein Ra and Rb are both alkyl such as methyl or ethyl, obtained by an analogous procedure to process (b) herein. The hydrolysis or alcoholysis will normally be carried out at a temperature in range 10° to 80° C. using an aqueous mineral acid such as hydrochloric acid in an alkanol (such as ethanol or 2-propanol) or an ether (such as tetrahydrofuran) as solvent.

The starting materials of formula IV wherein one of $Q^1$ and $Q^2$ is hydrogen and the other is a group of the formula —CRaRb.OH are intermediates in the above-mentioned formation of the starting materials of formula IV wherein $Q^1$ and $Q^2$ are both hydrogen. However, said intermediates are not normally isolated or characterised. Accordingly, the invention also provides a modification of process (c) which comprises reacting a compound of formula V wherein one of Ra and Rb is hydrogen, methyl or ethyl and the other is methyl or ethyl (preferably Ra=Rb=methyl or ethyl) with an excess of an aldehyde of the formula R.CHO (or a hydrate, acetal or hemiacetal thereof) in the presence of an acid catalyst (such as one of those given above), conveniently at a temperature in the range, for example, 10° to 80° C. and optionally in the presence of a suitable solvent or diluent (such as one of those given above).

The starting materials for use in the above processes may be made by general procedures of organic chemistry, known for the preparation of structurally related compounds. Thus, the aldehydes of formula III may be obtained, for example, by the method shown in Scheme I. The protected phenol derivatives of formula II may be made, for example, by using an analogous procedure to process (b) above using an aldehyde analogous to that of formula III, but wherein the phenol group has been protected with the group R", such an aldehyde being made, for example, by carrying out the procedures of Scheme I omitting the deprotection step (ii). Those of the starting materials of formula V which are novel may be obtained using analogous procedures to those described in European patent application, publication No. 94239, or by the route illustrated in Example 5 hereinafter.

The necessary Wittig reagents may be obtained by conventional procedures, for example by treating the corresponding phosphonium halides with a strong base such as sodium hydride, lithium diisopropylamide, potassium t-butoxide or butyllithium. They are generally formed in situ just prior to carrying out the condensation process (b) above.

It will be understood that the acids of formula I may also be obtained by other conventional procedures well known in the art, for example by base catalysed hydrolysis of the corresponding esters, amides or nitriles.

When a salt of a compound of formula I is required, it may be obtained, for example, by reaction with the appropriate base affording a physiologically acceptable cation, or by any other conventional procedure.

Further, when an optically active form of a compound of formula I is required, one of the aforesaid processes may be carried out using an optically active starting material. Alternatively, the racemic form of a compound of formula I may be reacted with an optically active form of a suitable organic base, for example ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1-4C)alkanol, whereafter the optically active form of said compound of formula I may be liberated by treatment with acid using a conventional procedure for example using an aqueous mineral acid such as dilute hydrochloric acid.

Many of the intermediates defined herein are novel, for example those of formulae II, III, IV and V, and are provided as further, separate features of the invention, together with salts thereof. Several of the intermediates of formula II, in particular those wherein X=Y=H, R"=methyl and R=isopropyl, sec-butyl, isobutyl or t-butyl also possess potent $TXA_2$ antagonist properties.

As stated earlier, the acids of formula I are antagonists of one or more of the actions of $TXA_2$, for example certain of its actions on blood platelets, the vasculature and/or the lung. The antagonism may be demonstrated in one or other of the following standard tests:

(a) The rabbit aortic strip model devised by Piper and Vane (*Nature*, 1969, 223, 29-35) using as agonist a freshly prepared sample of $TXA_2$, generated by addition of arachidonic acid (25 μg) to citrated, platelet rich rabbit plasma (250 μl) and allowing the mixture to aggregate fully over 90 seconds before use; alternatively the $TXA_2$ mimetic agent known as U46619 (described by R. L. Jones et alia in "Chemistry, Biochemistry and Pharmacological Activity of Prostanoids" edited by S. M. Roberts and F. Scheinmann, at page 211; Pergamon Press, 1979) may be used as the agonist;

(b) a blood platelet aggregation test based on that described by Born (*Nature*, 1962, 194, 927-929) and involving:

(i) aggregating human, citrated, platelet-rich plasma by addition of the $TXA_2$ mimetic agent U46619 so that a dose-response curve is generated;

(ii) generating a dose-response curve for U46619 stimulated platelet aggregation in the presence of increasing amounts of test compound (generally in the range $10^{-5}M$ to $10^{-10}M$); and (iii) calculating a $K_B$ value indicating potency of $TXA_2$ antagonism for the test compound, averaged over several concentrations, from the calculated 50% response value for U46619 aggregation in the presence and absence of test compound; and (c) a bronchoconstriction test involving measuring the inhibition by a test compound of the bronchoconstriction induced in the Konzett-Rossler, anaesthetised guinea-pig model (as modified by Collier and James, *Brit. J. Pharmacol.*, 1967, 30, 283-307) by intravenous administration of the $TXA_2$ mimetic agent, U46619 and involving:

(i) obtaining a cumulative dose-response curve to U46619 induced bronchoconstriction by intravenous administration of constant volumes of increasing concentrations of U46619 (0.2-4 μg/kg) in physiological saline solution and expressing bronchoconstriction as the maximum of that theoretically obtainable with no air flow to the test animal;

(ii) generating a cumulative dose-response curve to U46619 induced bronchoconstriction at 30 minute intervals for 3 hours after oral dosing of test compound; and (iii) calculating a dose-ratio for the test compound (that is the ratio of concentration of U46619 required to cause 50% bronchoconstriction in the presence and absence of test compound) indicating the potency of $TXA_2$ antagonism.

The antagonism of the effects of $TXA_2$ on the vasculature may be demonstrated, for example in rats in the following manner:

(d) Male rats (Alderley Park strain) are anaesthetised with sodium pentobarbital and blood pressure is monitored at the carotid artery. The $TXA_2$ mimetic agent U46619 is administered intravenously via the jugular vein at 5 μg/kg to induce a 20-30 mmHg (2640-3940 pascal) increase in systolic blood pressure. The process is repeated twice to ensure adequacy of response. A test compound is then administered either intravenously (via the jugular vein) or orally (via a cannula) directly into the stomach and the animal is challenged with U46619, five minutes after dosing with test compound and then successively every ten minutes until the hypertensive effect of U46619 is no longer blocked.

Further, the antagonism of the effects of $TXA_2$ in vivo may be demonstrated, for example, by assessing the effects of a test compound on the aggregation of blood platelets obtained after administration of test compound to a test animal, such as a rabbit, rat, guinea pig or dog, using standard procedures similar to that described in (a) above. However, when the aggregation of dog platelets is being studied it is necessary to use a predetermined, threshold concentration of the platelet aggregation agent adenosine diphosphate (about $0.4-1.2\times10^{-6}M$) together with the $TXA_2$ mimetic agent, U46619.

Using the above test procedures (a)-(c), the following representative results have been obtained with the compounds of formula I ($X=Y=H$) wherein (i) R is isopropyl, (ii) R is t-butyl; or (iii) R is sec-butyl, respectively:

Test (a), $pA_2$ (±0.05): (i), 7.71; (ii), 7.86; (iii) 7.80;

Test (b), $K_B$: (i), $1.79\times10^{-8}M$; (ii), $1.31\times10^{-8}M$; (iii) $1.34\times10^{-8}M$;

Test (c), dose ratio: (i)>75; (ii), >110; (iii), >75; 2 hours after oral dosing at 0.05 mg/kg.

Similarly, using test procedure (d) referred to above, the following representative results were obtained on inhibition of U46619 induced hypertension with the compounds of formula I referred to above:

compound (i): >70% inhibition 1 hour after oral dose of 0.5 mg/kg;

compound (ii): >75% inhibition 1 hour after oral dose of 0.1 mg/kg;

compound (iii): >70% inhibition 1 hour after oral dose of 0.5 mg/kg.

In general, other compounds of formula I and II show similar levels of $TXA_2$ antagonist properties in one or more of the above mentioned tests e.g. test (a) $A_2>7.0$; test (b) $K_B$: $>1.0\times10^{-7}M$; test (c) dose ratio >5, 2 hours after oral dosing at 0.1 mg/kg and/or test (d), significant inhibition of U46619 induced hypertension for at least 1 hour following oral dosing at 5 mg/kg or less.

By way of comparison, the structurally closely related compound 5(Z)-7-([2,4,5-cis]-2-isopropyl-4-phenyl-1,3-dioxan-5-yl)heptenoic acid disclosed, inter alia, in European patent application, publication No. 94239 possesses signficantly lower $TXA_2$ antagonist properties. Thus, for example, using test procedure (a) above, it has a $pA_2$ value of 5.9.

The above results indicate the unexpectedly superior $TXA_2$ antagonist properties possessed by the compounds of formula I.

As stated previously, the acids of formula I may be used in the therapy or prevention of diseases or adverse conditions in warm-blooded animals in which it is desirable to antagonise one or more of the actions of $TXA_2$. In general, an acid of formula I will be administered for this purpose by an oral, rectal, intravenous, subcutaneous, intramuscular or inhalation route, so that a dose in the range, for example 0.01-5 mg/kg body weight, will be given up to four times per day, varying with the route of administration, the severity of the condition and the size and age of the patient under treatment, according to principles well known in the art.

The acids of formula I will generally be used in the form of a pharmaceutical composition comprising a compound of formula I or, a pharmaceutically acceptable salt thereof as defined hereinabove, together with a pharmaceutically acceptable diluent or carrier. Such a composition is provided as a further feature of the invention and may be in a variety of dosage forms. For example, it may be in the form of tablets or capsules, or a solution or suspension, for oral administration; in the form of a suppository, for rectal administration; in the form of a sterile solution or suspension, for administration by intravenous or intramuscular injection; in the form of an aerosol or a nebuliser solution or suspension, for administration by inhalation; and in the form of a powder, together with pharmaceutically acceptable inert solid diluents such as lactose, for administration by insufflation.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The pharmaceutical compositions of the invention may also contain one or more agents known to be of value in diseases or conditions intended to be treated; for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

In addition to their use in therapeutic medicine, the acids of formula I are also useful as pharmacological tools in the development and standardisation of test systems for the evaluation of the effects of $TXA_2$ in laboratory animals such as cats, dogs, rabbits, monkeys, rats and mice, as part of the search for new therapeutic agents. The acids of formula I may also be used because of their $TXA_2$ antagonist properties in helping to maintain the viability of blood and blood vessels in warm-blooded animals (or parts thereof) under-going artificial extracorporeal circulation, for example during limb or organ transplants. When used for this purpose an acid of formula I, or a physiologically acceptable salt thereof, will generally be administered so that a steady state concentration in the range, for example, 0.1 to 10 mg per litre is achieved in the blood.

The invention will now be illustrated in the following non-limiting Examples in which, unless otherwise stated:

(i) evaporations were carried out by rotary evaporation in vacuo;

(ii) operations were carried out at room temperature, that is in the range 18°–26° C. and under an atmosphere of an inert gas such as argon;

(iii) flash column chromatography and medium pressure liquid chromatography (MPLC) were performed on Merck Kieselgel (Art. 9385) obtained from E. Merck, Darmstadt, W. Germany;

(iv) yields are given for illustration only and are not necessarily the maximum attainable;

(v) proton NMR spectra were normally determined at 90 or 200 MHz in $CDCl_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet;

(vi) all end-products were isolated as racemates.

EXAMPLE 1

A stirred solution of 4(Z)-6-([2,4,5-cis]-2-t-butyl- 4-o-methoxyphenyl-1,3-dioxan-5-yl)hexenoic acid (1.026 g) in dry tetrahydrofuran (THF) (5 ml) was treated at 4° C. under argon with a solution of lithium diphenylphosphide [prepared by treating chlorodiphenylphosphine (1.99 g) with lithium metal (252 mg) in dry THF (10 ml)]. The mixture was stirred for 5 minutes at 4° C., then for 3 hours at 50° C., then cooled to 10° C. and poured into an ice-water mixture (100 ml). The aqueous mixture was washed with ether (2×50 ml). The aqueous phase was acidified to pH 5 with acetic acid and extracted with ether (3×50 ml). These extracts were washed successively with water (2×50 ml) and saturated brine (50 ml), then dried ($MgSO_4$) and evaporated. The oil obtained was purified by MPLC, eluting with hexane/ethyl acetate/acetic acid (85:15:1 v/v), to give an oil which crystallised on standing, yielding 4(Z)-6-([2,4,5-cis]-2-t-butyl-4-o-hydroxyphenyl-1,3-dioxan-5-yl)hexenoic acid (0.859 g), m.p. 95°–98° C.; NMR: 1.00 (9H,s), 1.62 (1H, m), 1.87 (1H, m), 2.33 (4H, m), 2.63 (1H, m), 3.87 (1H, dt J=11, 1 Hz), 4.11 (1H, dd J=11, 1 Hz), 4.37 (1H, s), 5.21 (1H, d J=2 Hz), 5.29 (1H, m), 5.44 (1H, m), 6.88 (3H, m), 7.18 (1H, m), 8.40 (1H, br); m/e 348(M+).

The necessary starting material was obtained as follows: (i) A solution of (4-o-methoxyphenyl-2,2-dimethyl-1,3-dioxan-cis-5-yl)acetaldehyde (15.8 g) in dry THF (75 ml) was added under argon to a stirred, ice-cooled solution of the ylid prepared from (3-carboxypropyl)triphenylphosphonium bromide (51.48 g) and potassium t-butoxide (26.88 g) in dry THF (400 ml). The mixture was stirred for 15 minutes at 4° C., then for 1.5 hours at ambient temperature and was then poured into ice-water (1 liter). The mixture obtained was washed with 50% v/v ether/hexane (2×250 ml) to remove the bulk of neutral material. The aqueous phase was acidified to pH 5 with acetic acid and extracted with ether (4×300 ml). These extracts were washed successively with water (3×150 ml) and saturated brine (2×100 ml), then dried ($MgSO_4$) and evaporated. The residue was purifed by flash chromatography, eluting with toluene/ethyl acetate/acetic acid (80:20:2 v/v). The solid obtained was recrystallised from 10% ethyl acetate/hexane (250 ml) to give 4(Z)-6-(4-o-methoxyphenyl-2,2-dimethyl-1,3-dioxan-cis-5-yl)hexenoic acid (A) (13.0 g), m.p. 99°–101° C.; NMR: 1.52 (3H, s), 1.54 (1H, m), 1.56 (3H, s), 1.80 (1H, m), 2.28 (4H, m), 2.49 (1H, m), 3.77 (1H, dd J=11, 1 Hz), 3.82 (3H, s), 4.16 (1H, dm J =11 Hz), 5.28 (2H, m), 5.45 (1H, d J=2 Hz), 6.83 (1H dd J=7, 1 Hz), 6.97 (1H, td J=7, 1 Hz), 7.22 (1H, td J=8, 1 Hz), 7.48 (1H, dm J=8 Hz).

(ii) A suspension of A (1.88 g) in 2,2-dimethylpropionaldehyde (5 ml) was treated with p-toluene sulphonic acid (5 mg). The mixture was then stirred for 18 hours and then ether (50 ml) was added. The mixture was extracted with 0.5 M potassium hydroxide (4×25 ml). The combined aqueous extracts were acidified to pH 5 (acetic acid) and then extracted with ether (3×50 ml). The combined extracts were washed successively with water (2×50 ml) and saturated brine (50 ml), then dried ($MgSO_4$) and evaporated. The residue was purified by MPLC eluting with hexane/ethyl acetate/ acetic acid (85:15:1 v/v). A clear oil was obtained which crystallised on standing to give 4-(Z)-6-([2,4,5-cis]-2-t-butyl-4-o-methoxyphenyl-1,3-dioxan-5-yl)hexenoic acid (2.276 g), m.p. 74°–77° C.; NMR: 0.98 (9H, s), 1.51 (1H, m), 1.80 (1H, m), 2.27 (4H, m), 2.45 (1H, m), 3.80 (3H,s), 3.85 (1H,dm J=11 Hz), 4.02 (1H, dd, J=11, 1 Hz), 4.37 (1H, s), 5.13 (1H, d J=2 Hz), 5.27 (2H, m), 6.83 (1H, dd J=7, 1 Hz), 6.97 (1H, td J=7, 1 Hz), 7.22 (1H, td J=7, 1.5 Hz), 7.45 (1H, dd J=7, 1.5 Hz).

EXAMPLE 2

Using a similar procedure to that described in Example 1, but starting from 4(Z)-6-[2,4,5-cis]-2-sec-butyl-4-o-methoxyphenyl-1,3-dioxan-5-yl)hexenoic acid and carrying out the reaction with lithium diphenylphosphide at ambient temperature for 16 hours after the initial stirring at 4° C., there was obtained 4(Z)-6-([2,4,5-cis-]-2-sec-butyl-4-o-hydroxyphenyl-1,3-dioxan-5-yl)hexenoic acid in 24% yield as an oil which slowly crystallised to give solid of m.p. 62°–63° C.; NMR: 0.94 (3H, t J=7 Hz), 1.02 (3H, 2d J=6 Hz), 1.26 (1H, m), 1.65 (3H, m), 1.87 (1H, m), 2.33 (4H, m), 2.66 (1H, m), 3.88 (1H, dm J=11 Hz), 4.10 (1H, dd J=11, 1.5 Hz), 4.62 (1H, 2d J=3 Hz), 5.21 (1H, d J=2 Hz), 5.27 (1H, m), 5.43 (1H, m), 6.87 (3H, m), 7.17 (1H, m); m/e 348 (M+).

The necessary starting material was prepared essentially as in Example 1, starting from 2-methylbutyraldehyde in place of 2,2-dimethylpropionaldehyde, and was obtained as a yellow oil in 47% yield; NMR: 0.94 (3H, t J=7 Hz), 1.02 (3H, 2d J=7 Hz), 1.27 (1H, m), 1.61 (3 H, m), 1.82 (1H, m), 2.30 (4H, m), 2.48 (1H, m), 3.80 (3H, s), 3.98 (1H, dm J=11 Hz), 4.05 (1H, dd J=11, 1 Hz), 4.63 (1H, 2d J=3 Hz), 5.17 (1H, br s), 5.29 (2H, m), 6.83 (1H, br d J=8 Hz), 6.98 (1H, td J=7,1 Hz), 7.23 (1 H, m), 7.45 (1H, dd J=8, 1 Hz).

EXAMPLE 3

Using a similar procedure to that described in Example 1, but starting from 4(Z)-6-([2,4,5-cis]-2-isobutyl-4-o-methoxyphenyl-1,3-dioxan-5-yl)hexenoic acid, carrying out the reaction with lithium diphenylphosphide at 45° C. for 5 hours after the initial stirring at 4° C., and using toluene/ethyl acetate/acetic acid (80:20:2 v/v) as the MPLC eluant, there was obtained 4(Z)-6-([2,4,5-cis]-4-o-hydroxyphenyl-2-isobutyl-1,3-dioxan-5-yl)hexenoic acid, as a pale yellow oil in 90% yield; NMR: 0.95 (6H, d J=7 Hz), 1.65 (3H, m), 1.87 (2H, m), 2.31 (4H, m), 2.62 (1H, m), 3.88 (1H, dm J=11 Hz), 4.09 (1H, dd J=11, 1 Hz), 4.79 (1H, t J=5 Hz), 5.21 (1H, d J=2 Hz), 5.36 (2H, m), 6.88 (3H, m), 7.20 (1H, m); m/e 348 (M+).

The necessary starting material was prepared essentially as in Example 1, starting from 3-methylbutyraldehyde and using toluene/ethyl acetate/acetic acid (80:20:2 v/v) as the eluant for flash chromatography of the crude product, and was obtained as an oil in 64% yield; NMR: 0.94 (6H, d J=6 Hz), 1.60 (3H, m), 1.87 (2H, m), 2.26 (4H, m), 2.42 (1H, m), 3.80 (3H, m), 3.91 (1H, dm J=11 Hz), 4.02 (1H, dd J=11, 1 Hz), 4.83 (1H, t J=5 Hz), 5.17 (1H, d J=2 Hz), 5.26 (2H, m), 6.83 (1H, dd J=7, 1 Hz), 6.97 (1H, td J=7, 1 Hz), 7.22 (1H, td J=7, 1 Hz), 7.43 (1H, dd J=7, 1 Hz).

EXAMPLE 4

A solution of 4(Z)-6-([2,4,5-cis]-2-isopropyl-4-o-methoxyphenyl-1,3-dioxan-5-yl)hexenoic acid (740 mg) in dry 1,3-dimethyl-3,4,5,6-tetrahydro-2-(1H)-pyrimidinone (DMPU) (5 ml) was added to a stirred solution of sodium thioethoxide (1.07 g) in dry DMPU (30 ml) at 140° C. under argon. The mixture was stirred for 1 hour, cooled to ambient temperature and poured into water (100 ml). The aqueous mixture was washed with dichloromethane (2×50 ml), acidified to pH3 with 2M hydrochloric acid, and extracted with ether (3×50 ml). These extracts were washed successively with water (2×50 ml) and saturated brine (50 ml), then dried (MgSO4) and evaporated. The residual oil was purified by MPLC, eluting with hexane/ethyl acetate/acetic acid (85:15:1: v/v) to give 4(Z)-6-([2,4,5-cis]-4-o-hydroxyphenyl-2-isopropyl-1,3-dioxan-5-yl)hexenoic acid as a pale yellow oil which slowly crystallised to give solid (0.516 g) of m.p. 69°–71° C.; NMR: 1.02 (3 H, d J=7 Hz), 1.04 (3H, d J=7 Hz), 1.65 (1H, m), 1.92 (2H, m), 2.31 (4H, m), 2.65 (1H, m), 3.88 (1H, dm J=11 Hz), 4.10 (1H, dd J=11, 1 Hz), 4.55 (1H, d J=3 Hz), 5.22 (1H, d J=2 Hz), 5.28 (1H, m), 5.44 (1H, m), 6.88 (3H, m), 7.17 (1H, m), 8.31 (1H, b), m/e 335 ([M++H]).

The necessary starting material was obtained as follows:

(i) A solution containing (4,5-cis)-5-allyl-4-o-methoxyphenyl-2,2-dimethyl-1,3-dioxane (51.6 g), water (120 ml) and 2M hydrochloric acid (5.0 ml) in THF (400 ml) was heated with stirring at 70° C. for 2 hours. The mixture was poured into water (1 liter), then extracted with ether (3×500 ml). The combined extracts were washed with water (2×250 ml), then with brine (2×250 ml), dried (MgSO4) and evaporated to give erythro-2-allyl-l-o-methoxyphenyl-1,3-propanediol (B) as a crystalline solid (43.69 g), m.p. 59°–60° C.

(ii) p-Toluenesulphonic acid (10 mg) was added to a stirred suspension of B (7.0 g) in a mixture of isobutyraldehyde (3.15 ml) and trimethylorthoformate (4.48 ml). The mixture was stirred for 18 hours and then ether (100 ml) was added. The solution was washed successively with saturated sodium bicarbonate solution (2×50 ml) and saturated brine (2×50 ml), then dried (MgSO4) and evaporated. The oil obtained was purified by flash chromatography eluting with toluene to give [2,4,5-cis]-5-allyl-2-isopropyl-4-o-methoxyphenyl-1,3-dioxane as a clear oil (C) (4.90 g); NMR (90 MHz): 1.03 (6H, d J=7 Hz), 1.79 (3H, m), 2.31 (1H, m), 3.82 (3H, s), 4.01 (1H dm J=11 Hz), 4.12 (1H, dd J=11 1.5 Hz), 4.55 (1H, d J=3 Hz), 4.90 (2H, m), 5.18 (1H, br s), 5.57 (1H, m), 6.81 (1H, dd J=7, 1.5 Hz), 6.97 (1H, td J=7, 1.5 Hz), 7.23 (1H, td J=7, 1.5 Hz), 7.47 (1H, dd J=7,2 Hz).

(iii) Ozone was passed through a solution of C (4.61 g) in dichloromethane (120 ml) at −78° C. until a permanent blue colour developed. The solution was then flushed with argon until colourless. A solution of triphenylphosphine (6.56 g) in dichloromethane (20 ml) was added and the mixture left at ambient temperature overnight. After evaporation of the solvent the residual cloudy oil was purified by flash chromatography, eluting with dichloromethane, to give ([2,4,5-cis]-2-isopropyl-4-o-methoxyphenyl-1,3-dioxan-5-yl)acetaldehyde, as a clear oil (D) (3.70 g); NMR (90 MHz): 1.00 (6H, d J=7 Hz), 1.91 (1H, m), 2.50 (3H, m), 3.80 (3H, s), 4.02 (2H, s), 4.50 (1H, d J=4 Hz), 5.13 (1H, br s), 6.75–7.50 (4H, m), 9.50 (1H, s).

(iv) A solution of D (1.39 g) in dry THF (20 ml) was added under argon with stirring and ice-cooling to a solution of the ylid prepared from (3-carboxypropyl)triphenylphosphonium bromide (5.4 g) and potassium t-butoxide (2.78 g) in dry THF (40 ml). The mixture was stirred for 1 hour at 4° C., then overnight at ambient temperature and was then poured into ice-water (100 ml). The aqueous mixture was washed with 50% v/v ether/hexane to remove the bulk of the neutral material. After acidification to pH3, the aqueous phase was extracted with ether (3×50 ml). The extracts were washed successively with water (2×50 ml) and saturated brine (50 ml), then dried (MgSO4) and evaporated. The yellow oil obtained was purified by MPLC, eluting with hexane/ethyl acetate/acetic acid (85:15:1 v/v) to give 4(Z)-6-([2,4,5-cis]-2-isopropyl-4-o-methoxyphenyl-1,3-dioxane-5-yl)hexenoic acid, as a clear oil (0.993 g); NMR: 1.02 (3H, d J=7 Hz), 1.04 (3H, d J=7 Hz), 1.57 (1H, m), 1.90 (2H, m), 2.31 (4H, m), 2.48 (1H, m), 3.80 (3H, s), 3.90 (1H, dm J=11 Hz), 4.05 (1H, dd J=1 Hz), 4.55 (1H, d J=3.5 Hz), 5.16 (1H, d J=2 Hz), 5.29 (2H, m), 6.83 (1H, dd J=7, 1 Hz), 6.97 (1H, td J=7, 1 Hz), 7.23 (1H, td J=7, 1.5 Hz), 7.46 (1H, dd J=7, 1.5 Hz).

EXAMPLE 5

A mixture containing 4(Z)-6(4-[5-fluoro-2-hydroxyphenyl]-2,2-dimethyl-1,3-dioxan-cis-5-yl)hexenoic acid (423 mg), isobutyraldehyde (3 ml) and p-toluenesulphonic acid (2 mg) was stirred at room temperature for 1 hour. The whole reaction mixture was purified by flash column chromatography, eluting with hexane/ethyl acetate/acetic acid (85:15:2 v/v), to give 4(Z)-6-([2,4,5-cis]-4-[5-fluoro-2-hydroxyphenyl]-2-isopropyl-1,3-dioxan-5-yl)hexenoic acid (401 mg) as a colourless oil; NMR: 0.98 (3H, d J=7 Hz), 1.02 (3H, d J=7 Hz), 1.5-2.7 (8H, m), 3.9 (1H, dm J=12 Hz), 4.1 (1H, dd J=12, 1 Hz), 4.5 (1H, d J=4 Hz), 5.15 (1H, d J=3 Hz), 5.2-5.6 (2H, m) and 6.6-7.3 (3H, m).

The starting acid was obtained as follows:

(i) Triethylamine (42 ml) was added with stirring and cooling under an argon atmosphere to a solution containing 5-fluoro-2-methoxybenzaldehyde (23.1 g) [prepared as a white solid, m.p. 41°-43° C., by an analogous method to that described in U.S. Pat. No. 4367234] and anhydrous zinc chloride (45 g) in dry dichloromethane (250 ml) at such a rate that the reaction temperature did not exceed 25° C. Stirring was continued for 15 hours. The mixture was acidified to pH 2 with 2 M hydrochloric acid and extracted with ethyl acetate (3×150 ml). The combined extracts were washed with saturated brine (6×100 ml) and extracted with a saturated solution of sodium hydrogen carbonate (4×60 ml). The combined aqueous extracts were washed with ethyl acetate (50 ml), acidified to pH 2 using concentrated hydrochloric acid, and extracted with ethyl acetate (4×100 ml). These extracts were washed with saturated brine (6×50 ml), dried (MgSO4) and evaporated to give tetrahydro-2-(5-fluoro-2-methoxyphenyl)-5-oxo-3-furancarboxylic acid (40 g) as an oily mixture (E) of [2,3-cis] and [2,3-trans] diastereomers (39:61 by high pressure liquid chromatographic [HPLC] analysis); NMR: 2.93 (2H, d, J=8 Hz), 3.44 (1H, m), 3.88 (3H, s), 5.82 (1H, d, J=5, 7 Hz) and 7.10 (3H, m).

(ii) The diastereomeric mixture E (35 g) was added to a solution prepared from concentrated sulphuric acid (68 ml) and water (83 ml). The mixture was rapidly stirred for 72 hours. Water (160 ml) was added, with cooling, and the mixture was extracted with ethyl acetate (3×150 ml). The combined extracts were washed with saturated brine (6×100 ml), dried (MgSO4) and evaporated to give tetrahydro-2-(5-fluoro-2-methoxyphenyl)-5-oxo-3-furancarboxylic acid as a white solid (26.4 g; 14:86 [2,3-cis] to [2,3-trans] diastereomer by HPLC). Recrystallisation from toluene gave a further enrichment of the [2,3-trans] isomer (20.7 g; 8:92 cis: trans). This recrystallised material was added to a solution prepared from sulphuric acid (41 ml) and water (95 ml). The mixture was heated at 60° C. for 2.5 hours. Water (100 ml) was added and the mixture was extracted with ethyl acetate (3×100 ml). The combined extracts were washed with saturated brine (6×100 ml), dried (MgSO4) and evaporated to give [2,3-trans]-tetrahydro-2-(5-fluoro-2-methoxyphenyl)-5-oxo-3-furancarboxylic acid as a white solid (F) (20 g; containing 2% w/w [2,3-cis]diastereomer by HPLC analysis). (iii) A solution of borane-tetrahydrofuran complex (115 ml, 1M in tetrahydrofuran) was added to a stirred, ice-cooled solution of F (19.3 g) in dry THF (100 ml), under an atmosphere of argon. The mixture was allowed to warm to room temperature and stirring was continued for 15 hours. Water (40 ml) was added cautiously with cooling and the solvent was removed by evaporation. The residue was dissolved in ethyl acetate (100 ml). The solution obtained was washed successively with saturated potassium carbonate solution (20 ml) and saturated brine (50 ml), then dried (MgSO4) and evaporated to give [4,5-trans]-tetrahydro-5-(5-fluoro-2-methoxyphenyl)-4-hydroxymethylfuran-2-one as an oil (G) (20.5 g); NMR: 2.5-2.8 (3H, m), 3.6-4.0 (5H, m), 5.57 (1H, d J=5.5 Hz) and 6.68-7.06 (3H, m).

(iv) A solution of diisobutylaluminium hydride (114 ml, 1.5M in toluene) was added over 45 minutes to a stirred mixture containing G (20.2 g), dry toluene (90 ml) and dry 1,2-dimethoxyethane (22 ml) at −70° C. under argon. Stirring was continued for 2 hours. Methanol (3 ml) was then added and the mixture was allowed to warm to room temperature. Saturated brine (120 ml) and ethyl acetate (300 ml) were added. Insoluble material was removed by filtration. The organic layer was separated and the aqueous layer was extracted with ethyl acetate (100 ml). The combined ethyl acetate fractions were washed with saturated brine (2×100 ml), dried (MgSO4), and evaporated. The residual oil was purified by flash chromatography, eluting with petroleum ether (b.p. 40°-60° C.)/ethyl acetate (1:4 v/v), to give [2,3-trans]-tetrahydro-2-(5-fluoro-2-methoxyphenyl)-5-hydroxy-3-hydroxymethylfuran as a white solid (H) (9.2 g); NMR: 1.75-2.45 (3H, m), 3.65-4.05 (2H, m), 3.85 (3H, s), 4.45 (1H, t J=4 Hz), 5.25 (1H, d J=3 Hz), 5.65 (2H, br s) and 6.86-7.23 (3H, m).

(v) A mixture containing (3-carboxypropyl)triphenylphosphonium bromide (49.8 g), potassium t-butoxide (26.0 g) and dry toluene (300 ml) was stirred at 80° C. for 30 minutes under argon, and allowed to cool to room temperature. A solution of H (7.0 g) in dry tetrahydrofuran (40 ml) was added and stirring was continued for 1 hour. Water (140 ml) was added, with ice-water cooling, and the mixture was washed with ethyl acetate (3×60 ml). The aqueous phase was acidified to pH 5 with oxalic acid and extracted with ethyl acetate (3×100 ml). These extracts were combined, solid material removed by filtration and the filtrate evaporated. The residue was mixed with ether (100 ml) and residual solid removed by filtration. This filtrate was then extracted with a saturated solution of sodium hydrogen carbonate (3×100 ml). The combined extracts were washed with ethyl acetate (100 ml). The aqueous phase was then acidified to pH 5 with oxalic acid and extracted with ethyl acetate (3×100 ml). These combined extracts were washed with saturated brine (150 ml), dried (MgSO4) and evaporated to give erythro-4(Z)-8-hydroxy-7-hydroxymethyl-8-(5-fluoro-2-methoxyphenyl)octenoic acid as an oil (I) (9.0 g); NMR: 1.8-2.6 (7H, m), 3.75 (2H, m), 3.78 (3H, s), 5.2-5.5 (3H, m), 6.2 (3H, br s) and 6.7-7.3 (3H, m).

(vi) A mixture of I (6.3 g), p-toluenesulphonic acid (5 mg) and 2,2-dimethoxypropane (40 ml) was allowed to stand for 16 hours at ambient temperature. Triethylamine (3 drops) was added and the solvent was evaporated. The residual oil was purified by flash chromatography, eluting with toluene/ethyl acetate/acetic acid (85:15:2 v/v), to give 4(Z)-6-(4-[5-fluoro-2-methoxyphenyl]-2,2-dimethyl-1,3-dioxan-cis-5-yl)hexenoic acid as a colourless oil (J) (6.4 g); NMR: 1.45 (3H, s), 1.48 (3H, s), 1.6-2.5 (7H, m), 3.74 (3H, s), 3.62-3.78 (1H, dm, J=11 Hz), 4.02-4.13 (1H, dm J=11 Hz), 5.05-5.38 (2H, m), 5.3 (1H, d J=3 Hz) and 6.6-7.15 (3H, m).

(vii) Ethanethiol (4.4 ml) was added to a stirred suspension of sodium hydride (2.62 g, 50% w/w dispersion in mineral oil) in DMPU (80 ml) at 0° C. under argon. After 1 hour, the mixture was heated to 85° C. and then cooled to ambient temperature. A solution of J (3.52 g) in DMPU (20 ml) was added and the mixture was heated at 85° C. for 2 hours. The cooled mixture was poured into ice-water (160 ml) and extracted with dichloromethane (2×100 ml). The aqueous layer was acidified to pH 3 with 2M hydrochloric acid and extracted with ether (3×150 ml). The combined extracts were washed successively with water (2×100 ml) and saturated brine (100 ml), then dried (MgSO$_4$) and evaporated. The residual oil was purified by flash chromatography, eluting with toluene/ethyl acetate/acetic acid (80:20:2 v/v), to give 4(Z)-6-(4-[5-fluoro-2-hydroxyphenyl]-2,2-dimethyl-1,3-dioxan-cis-5-yl)hexenoic acid as a colourless oil (2.62 g); NMR: 1.5 (3H, s), 1.55 (3H, s), 2.2–2.8 (7H, m), 3.8 (1H, dd J=12, 1.5 Hz), 4.1 (1H, dm J=12 Hz), 5.1–5.6 (2H, m), 5.4 (1H, d J=3 Hz) and 6.7–7.3 (3H, m).

EXAMPLE 6

Using a similar procedure to that described in Example 5, but using an excess of 2,2-dimethylpropionaldehyde instead of isobutyraldehyde, there was obtained 4(Z)-6-([2,4,5-cis]-4-[5-fluoro-2-hydroxyphenyl-2-alpha,alpha-dimethylpropyl-1,3-dioxan-5-yl)hexenoic acid as a colourless oil in 81% yield; partial NMR: 6.62 (m, 3 aromatic H); 4.35 (1H, s, dioxan-C2); 5.15 (1H, d J=2 Hz, dioxan-C4); 1.0 (9H, s, CH$_3$.C).

EXAMPLE 7

Using a similar procedure to that described in Example 1, but starting from (−)-4(Z)-6-([2,4,5-cis]-2-t-butyl-4-o-methoxyphenyl-1,3-dioxan-5-yl)hexenoic acid there was obtained (−)-4(Z)-6-([2,4,5-cis]-2-t-butyl-4-o-hydroxyphenyl-1,3-dioxan-5-yl)hexenoic acid in 86% yield as a crystalline solid, m.p. 117°–118° C. Further recrystallisation from 10% v/v ethyl acetate/hexane gave material of m.p. 118°–119° C.; $^{23}[\alpha]_D$−166.9° (c 1.0, methanol), with an NMR spectrum essentially identical to that of the corresponding racemate (Ex. 1); m/e 348 (M+).

The necessary starting material was obtained as follows:

(i) Solid potassium t-butoxide (4.48 g) was added under argon to a stirred, ice-cooled mixture of (3-carboxypropyl)triphenylphosphonium bromide (6.44 g) and (−)-[2,3-trans]-tetrahydro-5-hydroxy-3-hydroxymethyl-2-o-methoxyphenylfuran (A) (2.24 g) in dry THF (75 ml). The mixture was stirred for 15 minutes at 4° C., then for 1 hour at ambient temperature and was then poured into ice-water (150 ml). The mixture obtained was washed with ether (2×50 ml) to remove the bulk of the neutral material. The aqueous phase was acidified to pH4 with 1M hydrochloric acid and extracted with ether (1×100 ml, 2×50 ml). These combined extracts were washed successively with water (2×50 ml) and saturated brine (2×50 ml), then dried (MgSO$_4$) and evaporated. The residue was purified by flash chromatography, eluting with ether/hexane/acetic acid (80:20:1 v/v) to give (−)-erythro-4(Z)-8-hydroxy-7-hydroxymethyl-8-o-methoxyphenyl-4-octenoic acid (B) as a colourless oil (2.76 g); $^{22}[\alpha]_D$−68.3° (c 1.1, methanol); NMR: 1.92 (1H,m), 2.0–2.6 (6H,m), 3.67 (2H,m), 3.82 (3H,s), 5.21 (1H,d J=5 Hz), 5.37 (2H,m), 6.87 (1H,dd J=8,1 Hz), 6.98 (1H,td J=7,1 Hz), 7.25 (1H,m), 7.42 (1H,dd J=7,1 Hz); m/e 294 (M+).

(ii) A solution of B (2.57 g) in 2,2-dimethoxypropane (8.5 ml) was treated with 'Amberlyst'-15 (Trademark of Rohm and Haas Company) strongly acid, macroreticular ion-exchange resin (0.5 g) and the mixture stirred for 2½ hours at ambient temperature. The solid was removed by filtration and washed with ether (10 ml). The filtrate and washings were concentrated in vacuo and the residue was purified by MPLC, eluting with hexane/ethyl acetate/acetic acid (80:20:1 v/v). A clear oil was obtained which slowly crystallised to give (−)-4(Z)-6-(4-o-methoxyphenyl-2,2-dimethyl-1,3-dioxan-cis-5-yl)hexenoic acid (C) (2.48 g). Recrystallisation from hexane gave solid of m.p. 71°–73° C. $^{23}[\alpha]_D$−145.5° (c 1.1, methanol); NMR spectrum essentially identical to that of the corresponding racemate (Compound A in Ex. 1);

(iii) A suspension of C (1.00 g) in 2,2-dimethylpropionaldehyde (2 ml) woodtreated with 'Amberlyst'-15 ion-exchange resin (0.1 g) and the mixture stirred for 3 hours at ambient temperature. Ether (10 ml) was added and the solid was removed by filtration. The filtrate was concentrated in vacuo and the residue was purified by MPLC using hexane/ethyl acetate/acetic acid (85:15:1 v/v) as eluant. The clear oil which was obtained, slowly crystallised to give (−)-4-(Z)-6-([2,4,5-cis]-2-t-butyl-4-o-methoxyphenyl-1,3-dioxan-5-yl)hexenoic acid (0.99 g), m.p. 101°–105° C., $^{23}[\alpha]_D$−162.8° (c, 1.0, methanol); NMR spectrum essentially identical to that of the corresponding racemate (described part (ii) of Ex. 1); m/e 363 (M+H)+.

The furan derivative A was itself obtained as follows:

(iv) A solution of d-ephedrine (61.2 g.) in hot ethyl acetate (150 ml.) was added to the solution of [2,3-trans]-tetrahydro-2-o-methoxyphenyl-5-oxo-3-furancarboxylic acid (87.6 g.) in hot ethyl acetate (350 ml.). The mixture was allowed to cool to room temperature during 2 hours and the crystalline salt which had formed was separated by filtration to give 62 g. of solid material having $^{25}[\alpha]_D$+40.2° (methanol). This material was recrystallised twice from ethyl acetate to give 48 g. of optically pure solid $^{25}[\alpha]_D$+50.3° (methanol). This solid was added to ethyl acetate (1 liter) and 2M hydrochloric acid (150 ml.). The ethyl acetate layer was washed with brine (2×100 ml.) until the pH of the washings was pH2–3, and then dried (MgSO$_4$) and evaporated. The residue was dissolved in boiling toluene (200 ml.). Insoluble material was removed by hot filtration. The filtrate was allowed to cool to give (+)-[2,3 trans]-tetrahydro-2-o-methoxyphenyl-5-oxo-3- furancarboxylic acid (D) (27.4 g.) $^{25}[\alpha]_D$+33.0° (methanol). Recrystallisation from toluene gave material of $^{25}[\alpha]_D$+33.8° (methanol), m.p. 125°–127° C.. (decomposition), shown to be >98% optically pure by conversion of a small sample to its (−)-amyl ester and examination of the $^{13}$C NMR spectrum.

(v) A solution of D (97.5 g.) in dry tetrahydrofuran (150 ml.) was cooled to 15° C. and treated with a solution of borane in tetrahydrofuran (500 ml.) of a 1M solution) with the temperature maintained at 20°–25° C. After 30 minutes the reaction was complete (as judged by TLC analysis) and water (200 ml.) was added slowly to decompose the excess borane. The mixture was concentrated in vacuo and the residue was mixed with ethyl acetate (500 ml.). The organic layer was washed successively with saturated potassium carbonate solution (2×100 ml.) and saturated brine, dried (MgSO$_4$), and evaporated to give [4,5-trans]-tetrahydro-4-hydroxymethyl-5-o-methoxyphenylfuran-2-one (E) as a viscous oil (81.8 g.), having $^{25}[\alpha]_D-14.2°$ (methanol) and a satisfactory NMR spectrum (d$_6$-acetone): 2.6 (3H,m), 3.7 (2H,m), 3.8 (3H,s), 4.1 (1H,br), 5.55 (1H,m), 6.8-7.5 (4H,m).

(vi) A solution of E (obtained above) in 1,2-dimethoxyethane (150 ml.) and dry toluene (500 ml.) was cooled under a nitrogen atmosphere to −60° C. A toluene solution of diisobutylaluminium hydride (672 ml. of 1.23M solution) was then added slowly. After 30 minutes the reaction was quenched by addition of methanol (50 ml.) and the mixture allowed to warm up to room temperature. 2M Hydrochloric acid (1 liter) and ethyl acetate (500 ml.) were then added and the mixture stirred. The aqueous phase was separated and extracted with ethyl acetate (2×500 ml.). The ethyl acetate phase and extracts were combined, dried (MgSO$_4$) and evaporated. The residual oil was dissolved in hot toluene (500 ml.). The solution obtained gave on cooling (−)-[2,3-trans]-tetrahydro-5-hydroxy-3-hydroxymethyl-2-o-methoxyphenylfuran (A) as a white solid (63.3 g.), $^{25}[\alpha]_D-24.2°$ (methanol), m.p. 110°-111° C.; NMR: 1.5-2.4 (3H,m), 3.4-4.0 (2H,m), 3.8 (3H,s), 4.2-4.8 (2H,br), 5.25 (1H,m), 5.6 (1H,m), 6.9-7.9 (4H,m).

The [2,3-trans]-tetrahydro-2-o-methoxyphenyl-5-oxo-3-furan-carboxylic acid requireed for (iv) was obtained as follows:

(a) Succinic anhydride (22 g.), o-methoxybenzaldehyde (20 g.) and anhydrous zinc chloride (44 g.) were added to dichloromethane (dried over alumina, 200 ml.) and the mixture stirred under argon. Triethylamine (41 ml.) was added to the ice-cooled mixture over a period of 20 minutes. The reaction mixture was then stirred at 20°-25° C. for 18 hours, after which time hydrochloric acid (2M,130 ml.) and ethyl acetate (200 ml.) were added. The subsequent mixture was stirred for 5 minutes. The aqueous phase was separated and extracted with ethyl acetate (150 ml.) The combined extracts were washed with saturated brine (50 ml.) and then extracted with saturated sodium bicarbonate solution (3×200 ml.). The combined aqueous extracts were washed with ethyl acetate, and then acidified to pH2 with concentrated hydrochloric acid. The oil which separated was extracted into ethyl acetate (2×150 ml.). The combined extracts were washed with saturated brine (4×50 ml.)until acid free, then dried (MgSO$_4$) and evaporated. Toluene (300 ml.) was added to the residue and the mixture was distilled atmospheric pressure until the residual material attained 110° C. On cooling to 20° C., tetrahydro-2o-methoxyphenyl-5-oxo-3-furancarboxylic acid separated as a crystalline white solid (27.2 g., 78%) (m.p. 106° C.) which was shown by NMR to be a mixture of [2,3-cis-]- and [2,3-trans]-isomer: 2.8-3.0 (2H,m), 3.1-3.6 (1H,m), 3.8 (3H,s), 5.82 (¾ H,d) [trans], 5.95 (1θH, d) [cis], 6.8-7.5 (4H,m). (b) A mixture of [2,3-cis]- and [2,3-trans]-tetrahydro-2-o-methoxyphenyl-5-oxo-3-furancarboxylic acid (188.6 g.) was added to an ice cooled solution of concentrated sulphuric acid (320 ml.) in water (480 ml.) and stirred at 20°-25° C. for 18 hours. Water (800 ml.) was then added and the mixture extracted with ethyl acetate (2×750 ml.). The combined extracts were washed with brine (4×500 ml.) until acid free, dried (MgSO$_4$) and evaporated to low volume. Toluene (1 liter) was added and the distillation continued at atmospheric pressure until the residual material attained a temperature of 110° C. On cooling pure [2,3-trans]-tetrahydro-2-o-methoxyphenyl-5-oxo-3-furancarboxylic acid separated as a white crystalline solid (169.5 g.,90%), m.p. 133°-134° C. ; NMR: 2.8-3.0 (2H,d), 3.3-3.6 (1H,m), 3.8 (3H,s), 5.82 (1H,d), 6.8-7.4 (4H,m).

EXAMPLE 8

Illustrative pharmaceutical dosage forms include the following tablet and capsule formulations, which may be obtained using standard procedures:

|  | mg/tablet |
|---|---|
| TABLET I | |
| Compound X* | 5.0 |
| Lactose Ph. Eur | 89.25 |
| Croscarmellose sodium | 4.0 |
| Maize starch paste (5% w/v paste) | 0.75 |
| Magnesium stearate | 1.0 |
| TABLET II | |
| Compound X* | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| CAPSULE | |
| Compound X* | 10 |
| Lactose Ph. Eur. | 488.5 |
| Magnesium stearate | 1.5 |

Note: Compound X* stands for a compound of formula I, or a salt thereof, for example a compound of formula I described in any of the previous Examples.

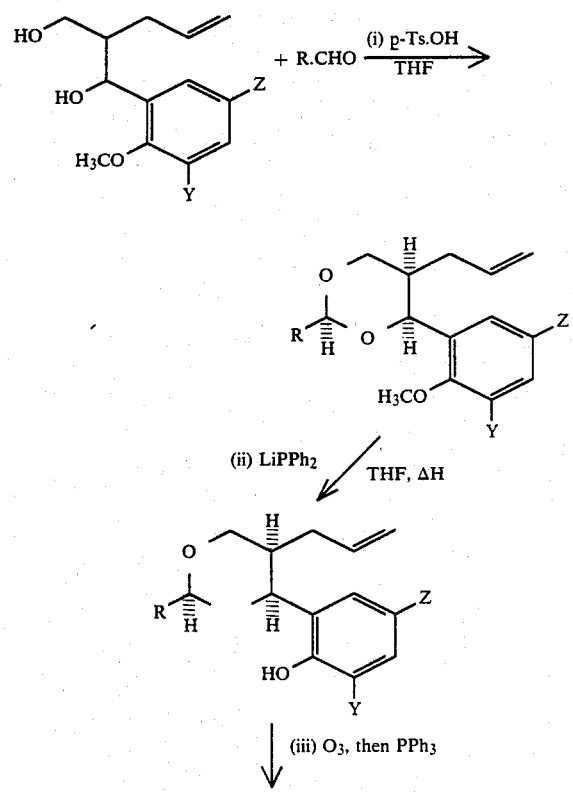

Scheme I

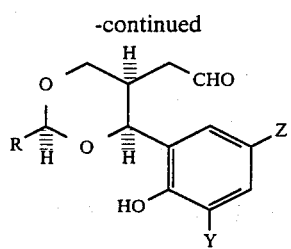

II

Formulae

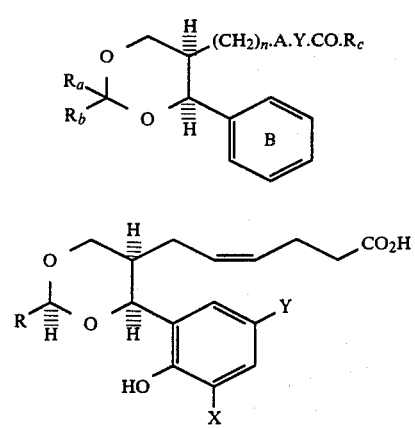

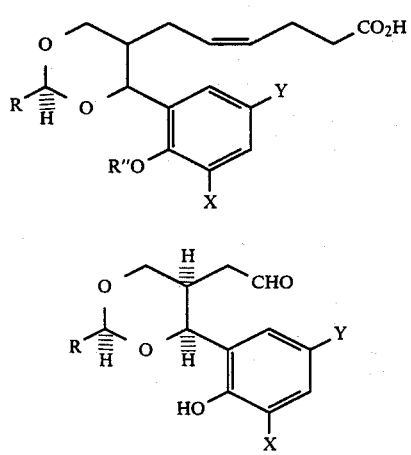

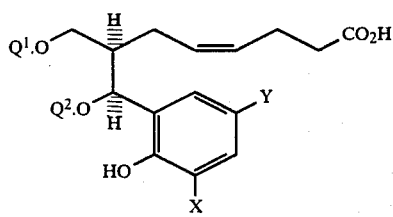

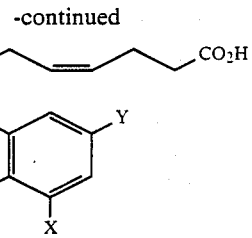

What is claimed is:

1. A hexenoic acid of the formula I

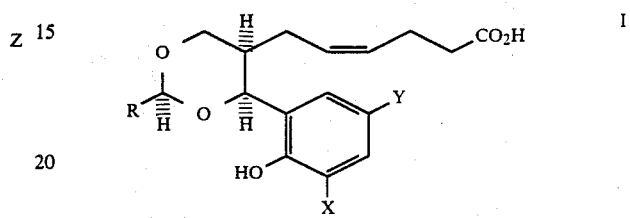

wherein R is branched alkyl of 3 to 5 carbon atoms; and one of X and Y is hydrogen or fluorine and the other is hydrogen; and wherein the groups at positions 2, 4 and 5 have cis-relative stereochemistry; or a pharmaceutically acceptable salt thereof.

2. A compound as claimed in claim 1 wherein R is selected from isopropyl, isobutyl, sec-butyl and t-butyl.

3. A compound as claimed in claim 1 or 2 wherein X is hydrogen and Y is hydrogen or fluoro.

4. A hexenoic acid of formula I as claimed in claim 1 wherein R is isopropyl, isobutyl, sec-butyl or t-butyl, and X and Y are hydrogen; and wherein the groups at positions 2, 4 and 5 of the dioxane ring have cis-relative sterochemistry; or a pharmaceutically acceptable salt thereof.

5. 4(Z)-6-([2,4,5-Cis]-2-t-butyl-4-o-hydroxyphenyl-1,3-dioxan-5-yl)hexenoic acid, or a pharmaceutically acceptable salt thereof.

6. A salt as claimed in claim 1 or 4 which is selected from alkali metal, alkaline earth metal, aluminium and ammonium salts, and from salts with organic amines and quaternary bases forming physiologically acceptable cations.

7. A method of antagonising one or more of the actions of thromboxane $A_2$ in a warm-blooded animal requiring such treatment which comprises administering to said animal an effective amount of a compound of the formula I, or a pharmaceutically acceptable salt thereof as defined in claim 1 or 4.

8. A pharmaceutical composition for antagonizing one or more of the actions of thromboxane $A_2$ in a warm-blooded animal which comprises an effective amount of a hexenoic acid of formula I or a pharmaceutical salt thereof, as claimed in claim 1 or 4, together with a pharmaceutically acceptable diluent or carrier.

* * * * *

UNITED STATES PATENT AND TRADEMARK OFFICE
CERTIFICATE OF CORRECTION

PATENT NO. : 4,772,625
DATED : September 20, 1988
INVENTOR(S) : Brewster et al

It is certified that error appears in the above-identified patent and that said Letters Patent is hereby corrected as shown below:

Column 16, Scheme I, please correct third formula to read:

--

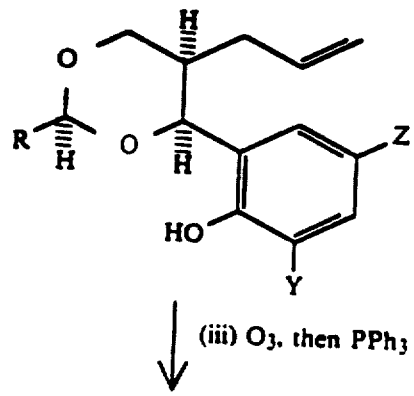

Signed and Sealed this

Twenty-seventh Day of June, 1989

Attest:

DONALD J. QUIGG

Attesting Officer

Commissioner of Patents and Trademarks